(12) United States Patent
Tanabe et al.

(10) Patent No.: US 9,568,336 B2
(45) Date of Patent: Feb. 14, 2017

(54) ELECTRONIC DEVICE

(71) Applicant: KYOCERA Corporation, Kyoto (JP)

(72) Inventors: Shigeki Tanabe, Kanagawa (JP); Hideki Morita, Kanagawa (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/164,893

(22) Filed: May 26, 2016

(65) Prior Publication Data
US 2016/0265936 A1 Sep. 15, 2016

Related U.S. Application Data

(63) Continuation of application No. 13/863,977, filed on Apr. 16, 2013, now Pat. No. 9,370,690.

(30) Foreign Application Priority Data

Apr. 16, 2012 (JP) ................. 2012-092890

(51) Int. Cl.
| | | |
|---|---|---|
| *G01P 15/00* | (2006.01) | |
| *G01P 13/00* | (2006.01) | |
| *G01C 22/00* | (2006.01) | |
| *A63B 24/00* | (2006.01) | |
| *A61B 5/11* | (2006.01) | |
| *A61B 5/00* | (2006.01) | |
| *G08G 1/052* | (2006.01) | |
| *G08G 1/056* | (2006.01) | |

(52) U.S. Cl.
CPC ........... *G01C 22/006* (2013.01); *A61B 5/0022* (2013.01); *A61B 5/1118* (2013.01); *A61B 5/6898* (2013.01); *A63B 24/00* (2013.01); *G01P 13/00* (2013.01); *G08G 1/052* (2013.01); *G08G 1/056* (2013.01); *A61B 5/1123* (2013.01); *A61B 5/4866* (2013.01)

(58) Field of Classification Search
CPC combination set(s) only.
See application file for complete search history.

(56) References Cited

U.S. PATENT DOCUMENTS

| | | |
|---|---|---|
| 8,793,098 B2 | 7/2014 | Fujiwara |
| 9,370,690 B2 * | 6/2016 | Tanabe .................. A63B 24/00 |

(Continued)

FOREIGN PATENT DOCUMENTS

| | | |
|---|---|---|
| JP | 2004-120688 A | 4/2004 |
| JP | 2010-81319 A | 4/2010 |
| JP | 2012-39333 A | 2/2012 |

OTHER PUBLICATIONS

Office Action in JP patent application No. 2012-092890, mailed Feb. 3, 2015.

*Primary Examiner* — Huan Tran
(74) *Attorney, Agent, or Firm* — Hauptman Ham, LLP

(57) ABSTRACT

A mobile telephone device includes a control unit that determines that a state is a state of walking or a movement state different from the state of walking, based on acceleration. In a case in which the control unit determines that a state is the movement state different from the state of walking, if a state immediately before determining the movement state different from the state of walking is the state of walking, the control unit makes the determination valid. As an example, the movement state different from the state of walking is a state of moving on a bicycle or a state of moving by transportation other than the bicycle.

11 Claims, 8 Drawing Sheets

(56) References Cited

U.S. PATENT DOCUMENTS

| | | |
|---|---|---|
| 2008/0027671 A1 | 1/2008 | Sano et al. |
| 2011/0208472 A1 | 8/2011 | Fujiwara |
| 2011/0282620 A1 | 11/2011 | Sakuraoka |
| 2013/0245470 A1 | 9/2013 | Izumida et al. |
| 2013/0245987 A1 | 9/2013 | Izumida et al. |
| 2013/0304414 A1 | 11/2013 | Levy et al. |
| 2013/0325392 A1 | 12/2013 | Takahashi |

\* cited by examiner

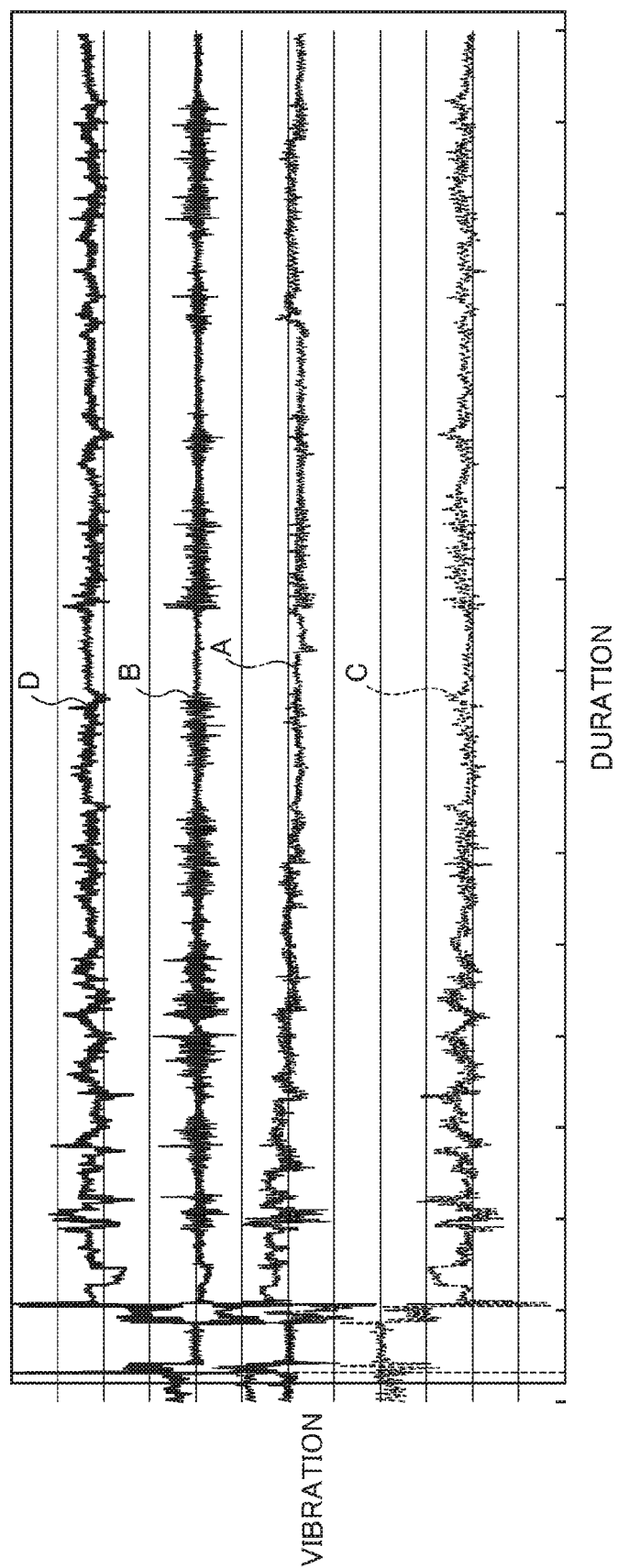

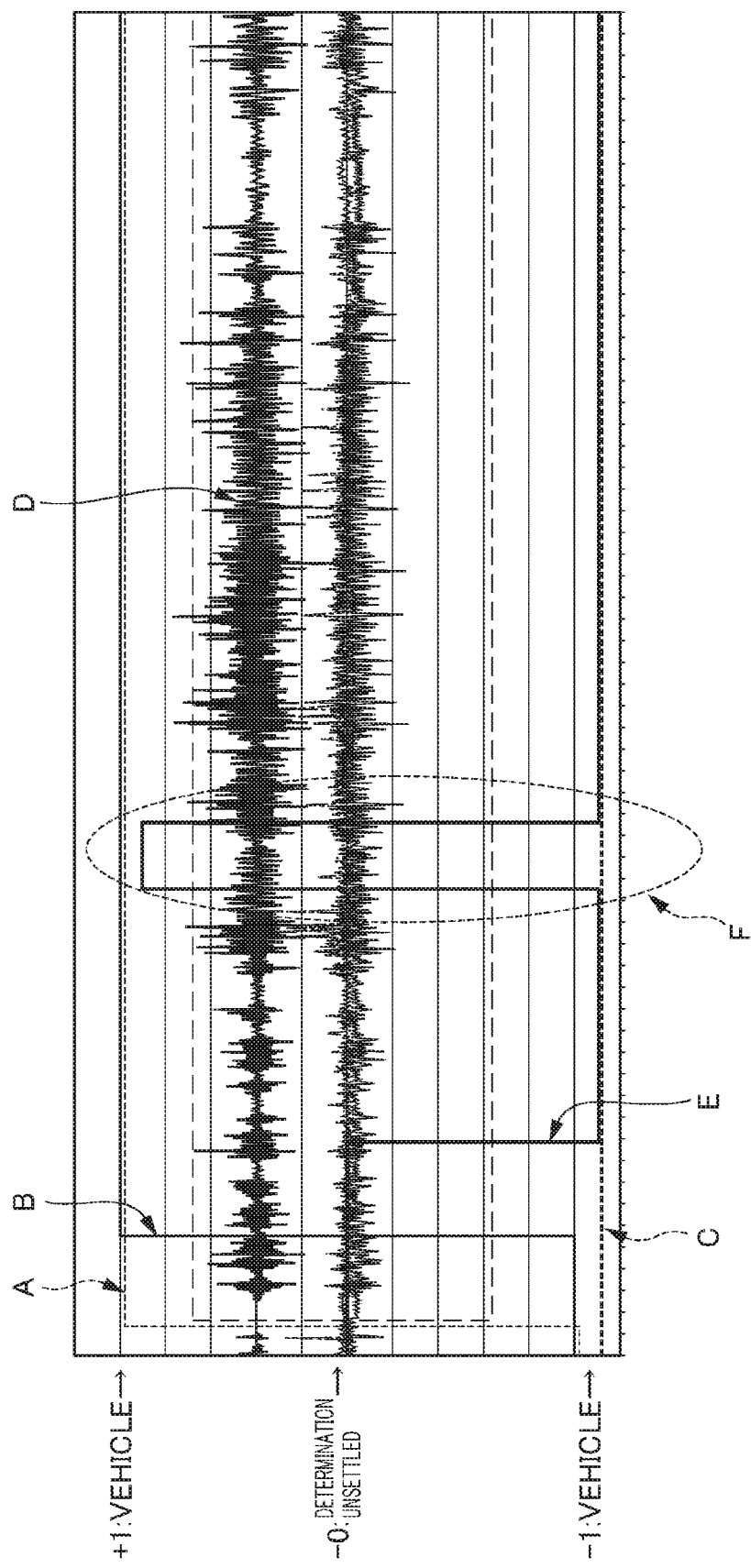

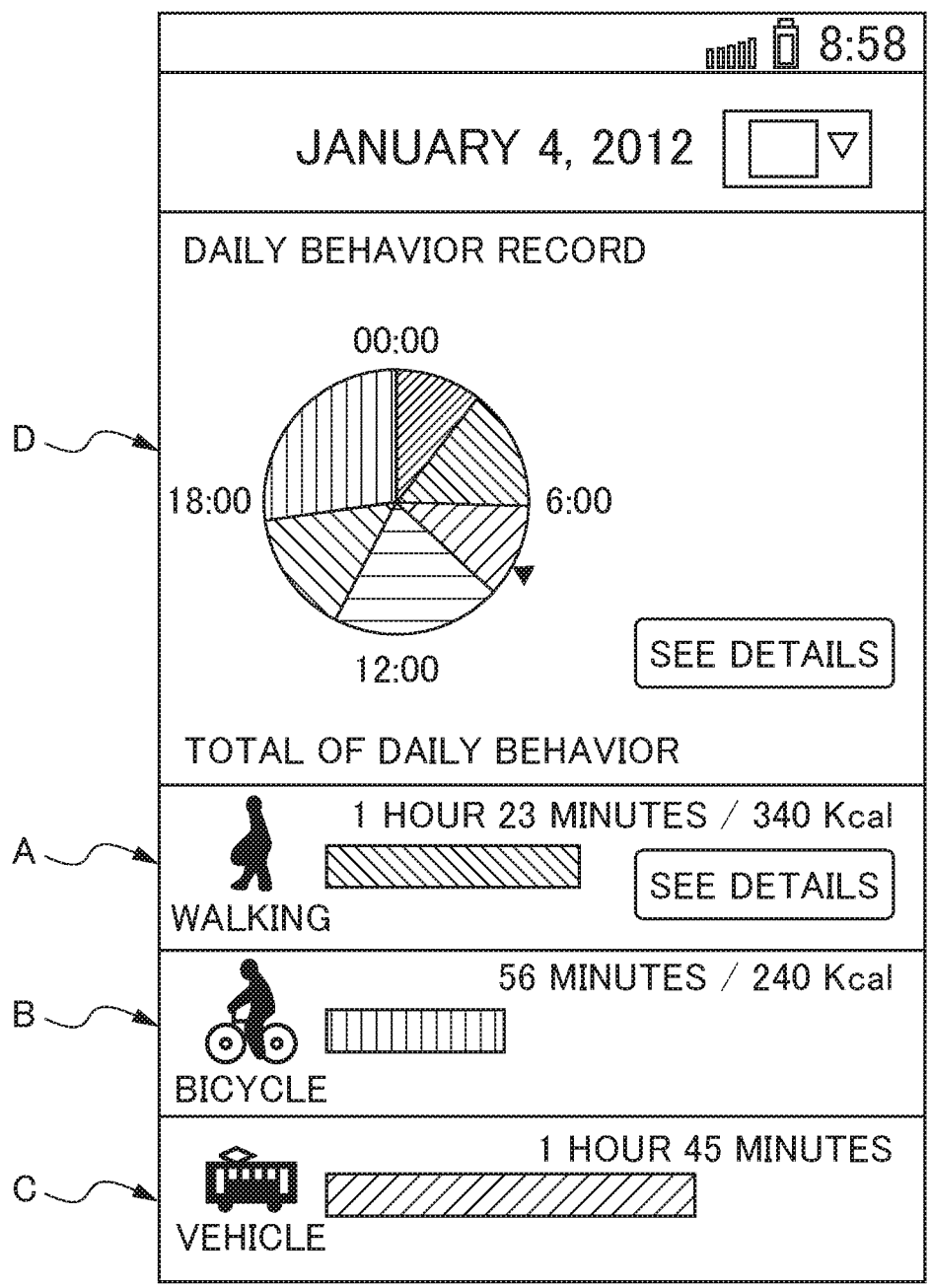

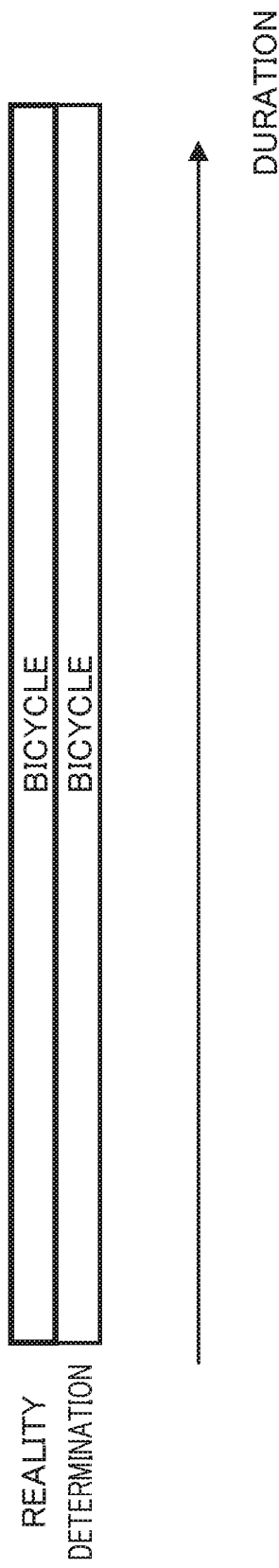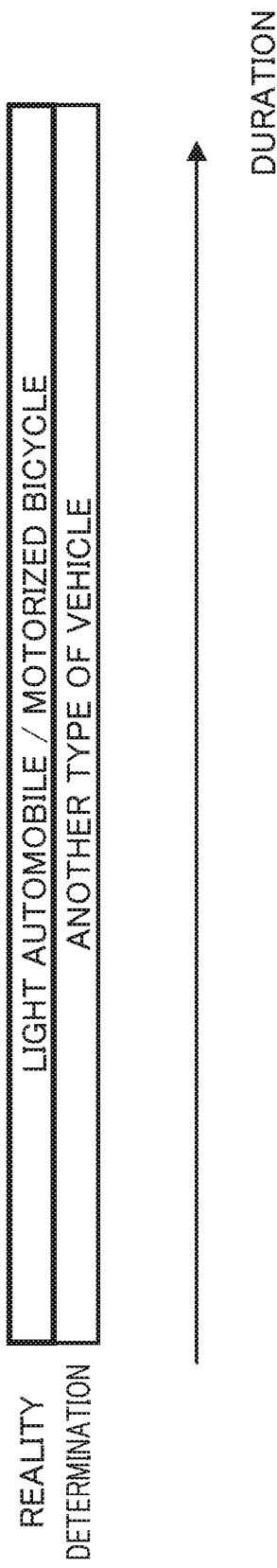

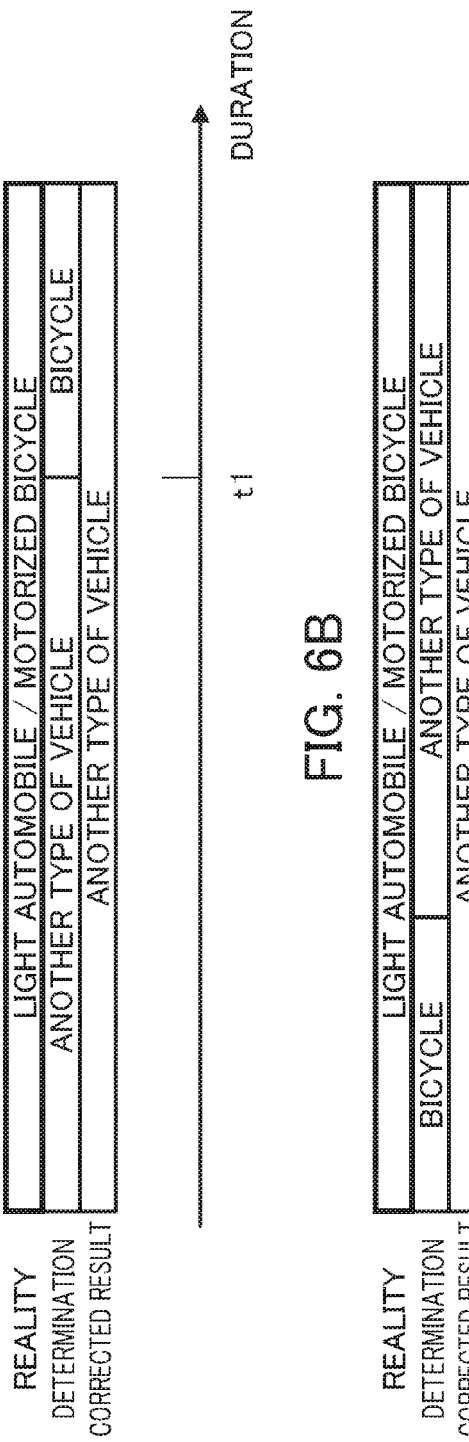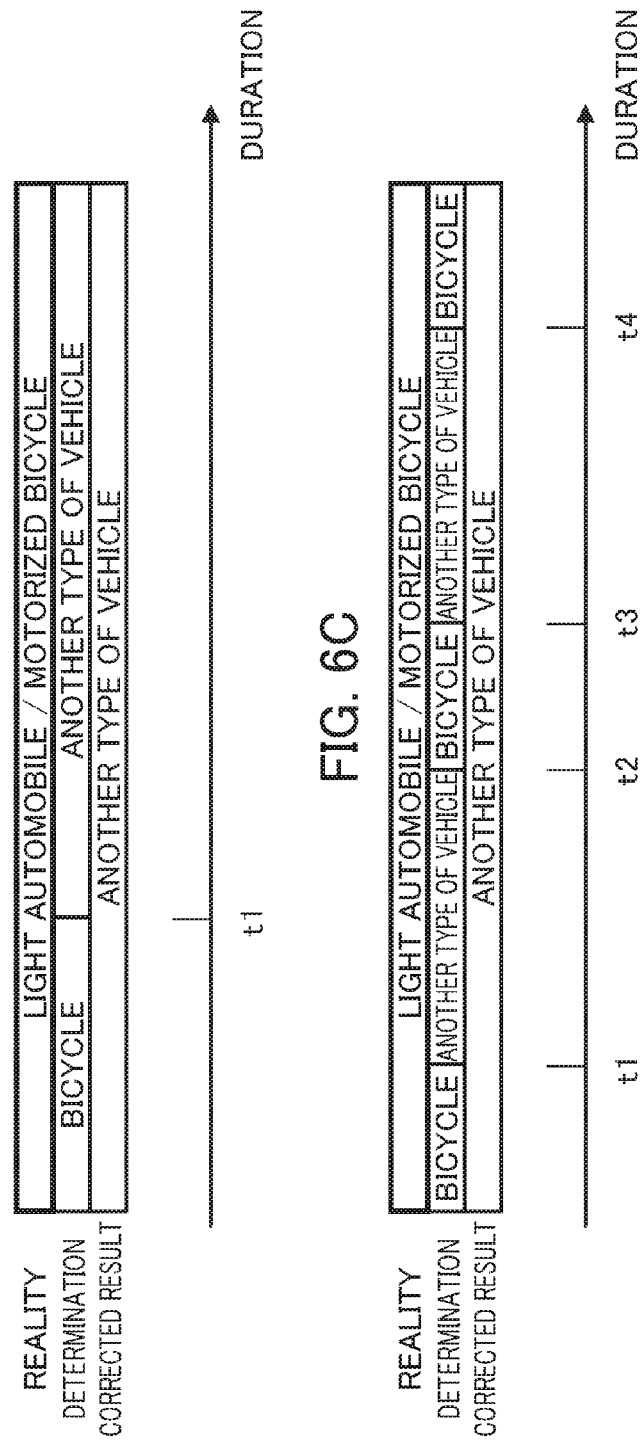

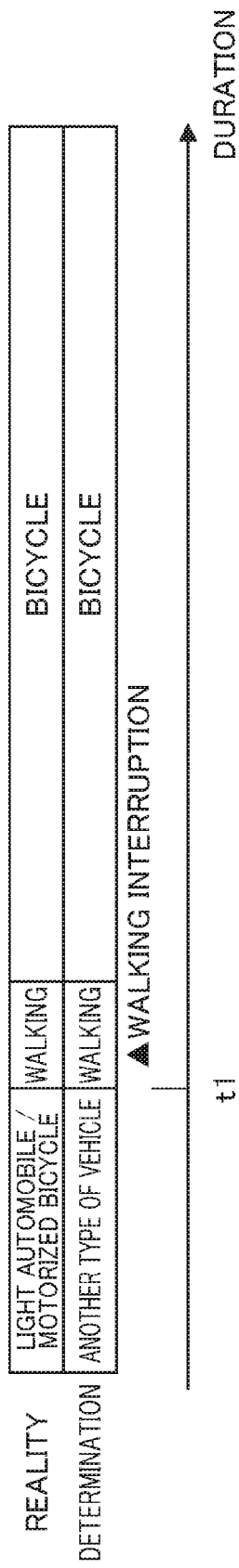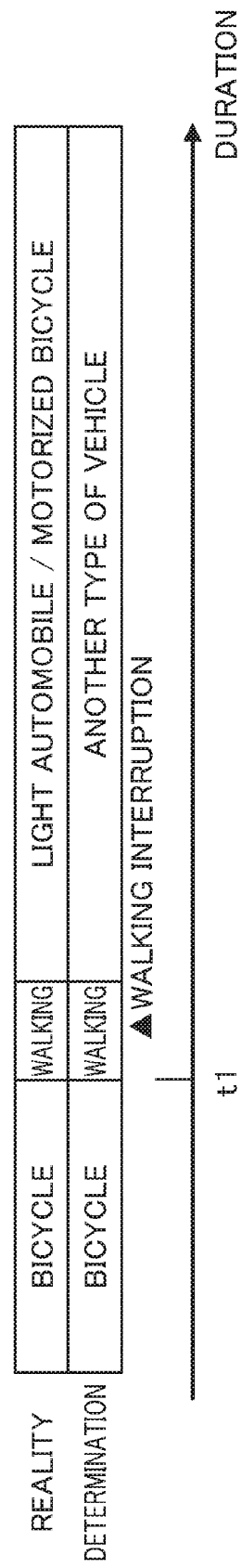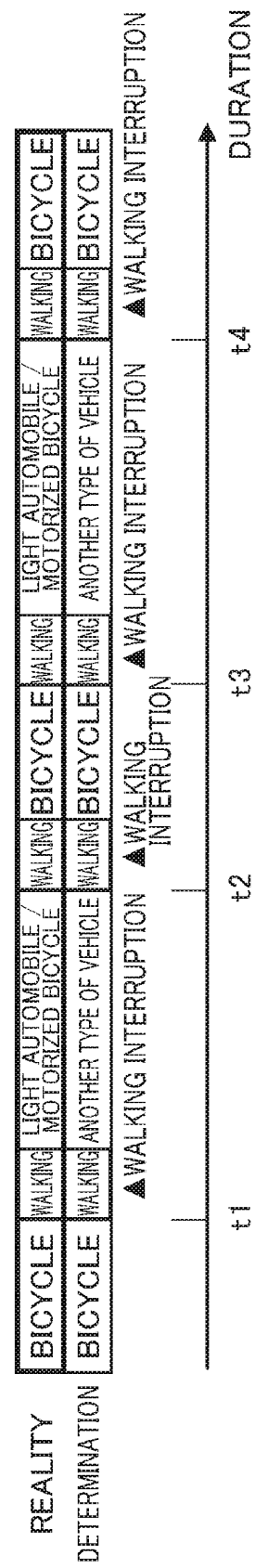

ELECTRONIC DEVICE

This application is a continuation of U.S. patent application Ser. No. 13/863,977, filed Apr. 16, 2013, which claims priority from Japanese Application No. 2012-092890, filed Apr. 16, 2012, the disclosures of which are hereby incorporated herein by reference herein in their entirety.

BACKGROUND OF THE INVENTION

Field of the Invention

The present invention relates to an electronic device having an acceleration sensor.

Related Art

Some electronic devices have a function of counting steps based on a value detected by an acceleration sensor (for example, see Japanese Unexamined Patent Application, Publication No. 2004-120688).

SUMMARY OF THE INVENTION

An object of the present invention is to provide an electronic device capable of detecting a plurality of states as well as a state of walking.

In order to solve the above problem, the electronic device according to the present invention includes a control unit that determines that a state is a state of walking or a movement state different from the state of walking, based on acceleration. In a case in which the control unit determines that a state is the movement state different from the state of walking, if a state immediately before determining the movement state different from the state of walking is the state of walking, the control unit makes the determination valid.

In order to solve the above problem, the electronic device according to the present invention includes a control unit that determines that a state is a state of walking or a movement state different from the state of walking, based on acceleration. In a case in which the control unit determines that a state is the movement state different from the state of walking, if a state immediately before determining the movement state different from the state of walking is not the state of walking, the control unit maintains the state immediately before determining the movement state different from the state of walking.

In order to solve the above problem, the electronic device according to the present invention includes a display unit; and a control unit that causes the display unit to display integrated duration of each of a state of walking and a movement state different from the state of walking, based on acceleration. In a case in which a state is changed to the movement state different from the state of walking, if incremented and integrated duration of the state of walking is not displayed immediately before the change, the control unit does not incrementally display integrated duration of the movement state different from the state of walking.

In the electronic device, the movement state different from the state of walking may be a state of moving on a bicycle or a state of moving by transportation other than the bicycle.

In order to solve the above problem, the electronic device according to the present invention includes a control unit that determines that a state is a first movement state as a state of walking, a second movement state different from the first movement state, or a third movement state different from the first movement state and the second movement state, based on acceleration. In a case in which the control unit determines that a state is the second movement state or the third movement state without the first movement state intervening therebetween, the control unit corrects the determination to the state, for which total determination duration is longer.

In order to solve the above problem, the electronic device according to the present invention includes a display unit; and a control unit that causes the display unit to display information of a first movement state as a state of walking, information of a second movement state different from the first movement state, and information of a third movement state different from the first movement state and the second movement state, based on acceleration. If the displaying of the information of the first movement state is not changed after changing the displaying of the information of the second movement state, the control unit does not change the displaying of the information of the third movement state.

In order to solve the above problem, the electronic device according to the present invention includes a control unit that recognizes a first movement state as a state of walking, a second movement state different from the first movement state, or a third movement state different from the first movement state and the second movement state, based on acceleration. The control unit recognizes the third movement state after recognizing the first movement state subsequent to the second movement state.

In the electronic device, the second movement state may be a state of moving on a bicycle, and the third movement state may be a state of moving by transportation other than the bicycle.

According to the present invention, a plurality of states as well as a state of walking can be detected.

BRIEF DESCRIPTION OF THE DRAWINGS

FIG. 2 is a diagram schematically showing a result of detection by an acceleration sensor;

FIG. 3 is a diagram illustrating determination of each state based on a result of detection by the acceleration sensor;

FIG. 4 is a view showing an aspect of displaying each state on a display unit;

FIG. 5A is a diagram showing comparison of an actual state with a result determined by the mobile telephone device;

FIG. 5B is a diagram showing comparison of an actual state with a result determined by the mobile telephone device;

FIG. 6A is a diagram showing comparison of an actual state with a result determined by the mobile telephone device;

FIG. 6B is a diagram showing comparison of an actual state with a result determined by the mobile telephone device;

FIG. 6C is a diagram showing comparison of an actual state with a result determined by the mobile telephone device;

FIG. 7A is a diagram showing comparison of an actual state with a result determined by the mobile telephone device;

FIG. 7B is a diagram showing comparison of an actual state with a result determined by the mobile telephone device;

FIG. 7C is a diagram showing comparison of an actual state with a result determined by the mobile telephone device.

DETAILED DESCRIPTION OF THE INVENTION

An embodiment for carrying out the present invention is described in detail with reference to the drawings. A mobile telephone device 1 is hereinafter described as an example of an electronic device.

Figure 1:
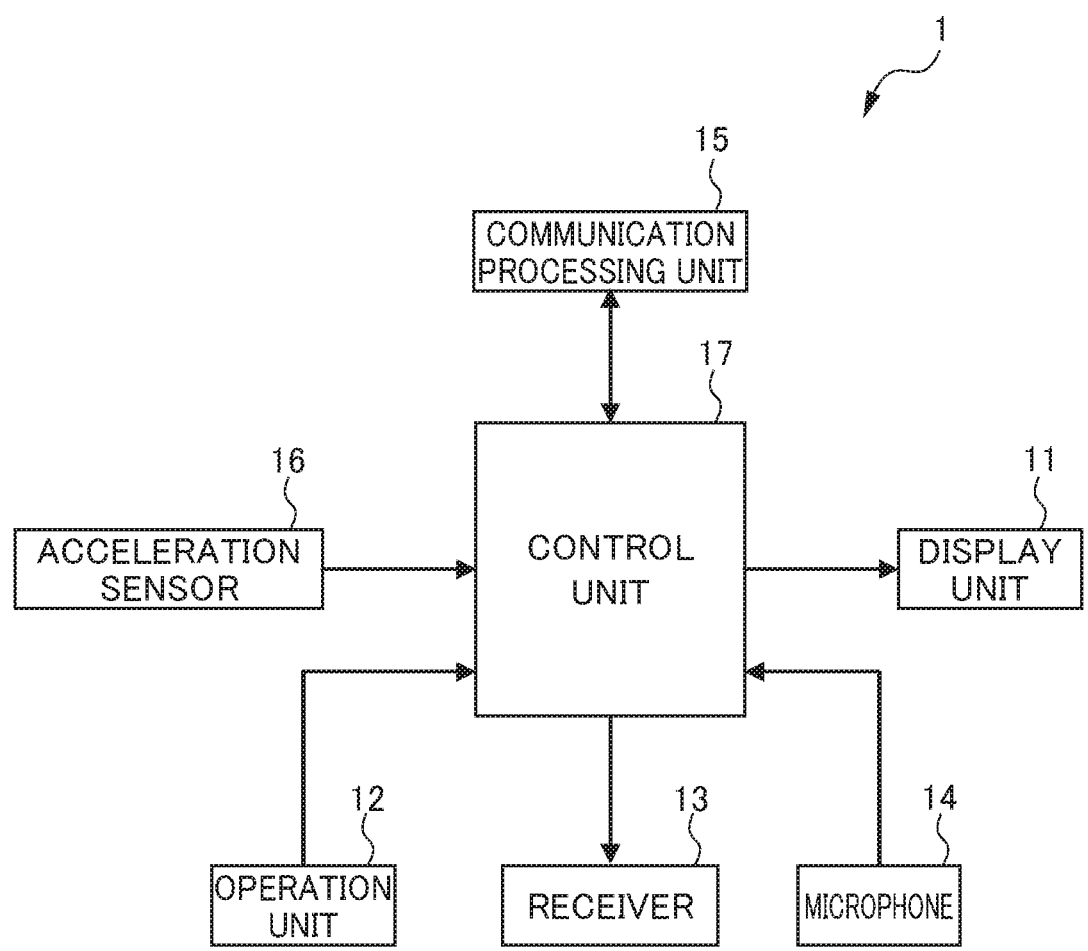
FIG. 1 is a block diagram showing a configuration of a mobile telephone device.

As shown in FIG. 1, the mobile telephone device 1 includes a display unit 11, an operation unit 12, a receiver 13, a microphone 14, a communication processing unit 15, an acceleration sensor 16, and a control unit 17.

The display unit 11 is configured by a display device such as a liquid crystal display or an organic electroluminescence panel. The display 11 displays characters, images, symbols, graphics and/or the like.

The operation unit 12 is configured by a plurality of buttons, and is operated by a user. The operation unit 12 may be configured by a single button.

When a sound signal is transmitted from the control unit 17, the receiver 13 converts the sound signal into sound to be output.

The microphone 14 converts sound such as the user's voice into a sound signal, and transmits the sound signal to the control unit 17.

The communication processing unit 15 includes an antenna 15a and a communication unit 15b. Communication methods implemented by the communication processing unit 15 are wireless communication standards. For example, the wireless communication standards include cellular telephone communication standards such as 2G, 3G and 4G.

The acceleration sensor 16 detects a direction and level of acceleration acting on the mobile telephone device 1, and outputs a result of detection to the control unit 17. The acceleration sensor 16 is of a three-axis (three-dimension) type for detecting acceleration in an X-axis direction, a Y-axis direction, and a Z-axis direction. For example, based on a force (F) externally applied to the mobile telephone device 1 and mass (m) of the mobile telephone device 1, the acceleration sensor 16 measures acceleration (a) (acceleration (a)=force (F)/mass (m)).

The acceleration sensor 16 is not limited to a piezoelectric sensor using a piezoelectric element, and may be configured by a sensor(s) such as an MEMS (Micro Electro Mechanical System) sensor of a piezoresistance type, an electrostatic capacity type, a heat sensing type, etc., a servo sensor that moves and returns a movable coil by way of a feedback electric current, and a strain gauge sensor that uses a strain gauge to measure strain occurring due to acceleration.

The control unit 17 controls the entirety of the mobile telephone device 1, and is configured to employ a central processing unit (CPU) and the like. Detailed descriptions of the control unit 17 will be provided later.

Here, descriptions are provided for processing by the control unit 17 to process a result of detection by the acceleration sensor 16.

As shown in FIG. 2, acceleration in the X-axis direction (A in FIG. 2), acceleration in the Y-axis direction (B in FIG. 2), acceleration in the Z-axis direction (C in FIG. 2), and a vector value synthesized from each acceleration (D in FIG. 2) are transmitted to the control unit 17 as a result of detection by the acceleration sensor 16. The control unit 17 determines a state of the mobile telephone device 1 by logging synthesized vector values and analyzing data thus logged.

Next, descriptions are provided for a case of applying the conventional art to an actual state and a state determined based on a result of detection by an acceleration sensor.

Case 1

First of all, descriptions are provided for a case of determining whether a user is riding in a vehicle. In the following descriptions, "+1" refers to a state of riding in a vehicle, and "−1" refers to a state of not riding in a vehicle.

This case assumes that the user is actually riding in a vehicle. Therefore, as shown in A in FIG. 3, if the state of not riding in a vehicle "−1" is changed to the state of riding in a vehicle "+1", such determination is considered to be correct.

A result shown in B in FIG. 3 (the state of riding in a vehicle "+1") was obtained from determination based on a result of detection by the acceleration sensor.

Based on this result, it is understood that the determination of whether the user is riding in a vehicle is correct.

Case 2

Next, descriptions are provided for a case of determining a type of a vehicle. In the following descriptions, "+1" refers to a state of riding on a bicycle, and "−1" refers to a state of using transportation other than a bicycle.

This case assumes that the user is actually using transportation other than a bicycle. Therefore, if a result as shown in C in FIG. 3 is obtained, the determination is considered to be correct. C in FIG. 3 is a result that was determined based on values detected by the acceleration sensor when the user was actually riding in a light automobile (D in FIG. 3).

A result shown in E in FIG. 3 was obtained from determination based on a result of detection by the acceleration sensor. In view of the results, after a certain period of time in which determination is unsettled, the state is changed to "−1" (the state of using transportation other than a bicycle), subsequently changed to "+1" (the state of riding on a bicycle), and subsequently changed back to "−1" (the state of using transportation other than a bicycle). The situation where the state was changed to "+1" (a portion F surrounded by a circle in FIG. 3) was actually a situation where the light automobile of the user jiggled due to a poor road surface condition.

In this way, in the conventional art, in a case of determining a vehicle by using an acceleration sensor, the user is incorrectly determined to be riding on a bicycle despite the user actually riding in an automobile, depending on the type of an automobile and the road surface condition affecting the amount of vibration.

Accordingly, the mobile telephone device 1 according to the present embodiment has a configuration of accurately detecting a plurality of states including a state of walking, without depending on a type of an automobile and a road surface condition affecting the amount of vibration. Descriptions are hereinafter provided for the configuration.

The control unit 17 determines that the state is a first movement state, a second movement state, or a third movement state, based on acceleration. According to such a configuration, in a case in which the control unit 17 determines that the state is the second movement state or the third movement state, if the state immediately before determining the second movement state or the third movement state is the first movement state, the control unit 17 makes the determination valid.

In other words, in a case in which the control unit 17 determines that the first movement state is changed to the second movement state or the third movement state, the control unit 17 makes the determination valid.

The first movement state is a state of walking. The second movement state is a state of moving on a bicycle (hereafter the second movement state is also a state of movement different from a state of walking). The third movement state is a state of moving by transportation (hereafter referred to as an automobile) other than a bicycle (hereafter the third movement state is also a state of movement different from a state of walking and the second movement state). These are examples, and the present invention is not limited thereto. The mobile telephone device 1 determines a state of walking, based on a result of detection by the acceleration sensor 16 using a pedometer function for counting steps.

In general, when the user transfers from a bicycle to an automobile, the user parks the bicycle in a bicycle-parking area, walks to a place where the automobile is parked, and rides on the automobile. Similarly, when the user transfers from an automobile to a bicycle, the user parks the automobile, walks to a place where the bicycle is parked, and rides on the bicycle. Therefore, a walking action intervenes, when the user transfers from a bicycle to an automobile, and when the user transfers from an automobile to a bicycle.

In a case in which the mobile telephone device 1 determines that the state is the second movement state or the third movement state, if the state immediately before the determination is the first movement state, the mobile telephone device 1 makes the determination valid. Therefore, the mobile telephone device 1 can reliably determine the states including a state of walking.

In a case in which the control unit 17 determines that the state is the second movement state or the third movement state, if the state immediately before determining the second movement state or the third movement state is not the first movement state, the control unit 17 maintains the state immediately before determining the second movement state or the third movement state.

For example, in a case in which the control unit 17 determines that the state of riding in an automobile is changed to the state of riding on a bicycle, since the state of walking does not intervene therebetween, the control unit 17 maintains the state of riding in an automobile.

Therefore, for example, in a situation where the user continues riding in an automobile, even if the automobile jiggles due to a poor road surface condition, the mobile telephone device 1 does not incorrectly determine that the user is riding on a bicycle, but can reliably determine the states including a state of walking.

The mobile telephone device 1 includes: the display unit 11; and the control unit 17 that causes the display unit 11 to display integrated duration of each of the first movement state, the second movement state, and the third movement state, based on acceleration.

According to such a configuration, in a case in which the state is changed to the second movement state or the third movement state, if incremented and integrated duration of the first movement state is not displayed immediately before the change, the control unit 17 does not incrementally display integrated duration of the second movement state or the third movement state.

For example, in a case in which the state of riding in an automobile is changed to the state of riding on a bicycle, if the state of walking does not intervene therebetween, the control unit 17 does not incrementally display integrated duration of the state of walking, and therefore does not incrementally display integrated duration of the state of riding on a bicycle, either. In this case, the control unit 17 incrementally displays integrated duration of the state of riding in an automobile.

Therefore, for example, in a situation where the user continues riding in an automobile, even if the automobile jiggles due to a poor road surface condition, the mobile telephone device 1 does not incorrectly determine that the user is riding on a bicycle, but can accurately incrementally display integrated duration of each state.

The mobile telephone device 1 includes: the display unit 11; and the control unit 17 that causes the display unit 11 to display information of the first movement state, the second movement state, or the third movement state, based on acceleration.

According to such a configuration, if the displaying of the first movement state is not changed after changing the displaying of the second movement state, the control unit 17 does not change the displaying of the third movement state; and if the displaying of the first movement state is not changed after changing the displaying of the third movement state, the control unit 17 does not change the displaying of the second movement state.

For example, as shown in FIG. 4, the control unit 17 causes the display unit 11 to display: an indicator A of the state of walking (hereinafter referred to as the indicator A); an indicator B of the state of riding on a bicycle (hereinafter referred to as the indicator B); and an indicator C of the state of riding in a vehicle (transportation such as an automobile and a train other than a bicycle) (hereinafter referred to as the indicator C).

The indicator A includes: integrated duration and its calories-out (1 hour 23 minutes/340 Kcal in the example shown in FIG. 4); and a schematic graph representing the integrated duration.

The indicator B includes: integrated duration and its calories-out (56 minutes/240 Kcal in the example shown in FIG. 4); and a schematic graph representing the integrated duration.

The indicator C includes: integrated duration (1 hour 45 minutes in the example shown in FIG. 4); and a schematic graph representing the integrated duration.

The control unit 17 causes the display unit 11 to display a pie chart D, in which the user's daily behavior record is sorted into the states by colors, respectively.

Since the mobile telephone device 1 visually displays the respective states in this manner, the user can grasp the daily behavior record (life log) at a glance.

In a case in which the indicator A is not changed after changing the indicator B, i.e. in a case in which the state of walking is not detected, the control unit 17 does not change the indicator C.

In other words, in a case in which the control unit 17 recognizes the state of riding on a bicycle based on a result of detection by the acceleration sensor 16, then changes (updates) the indicator B, and thereafter recognizes the state riding on a vehicle without recognizing the state of walking, the control unit 17 determines the recognition as misrecognition, and does not change the indicator C. In this case, the control unit 17 changes (updates) the indicator B.

In a case in which the indicator A is not changed after changing the indicator C, i.e. in a case in which the state of walking is not detected, the control unit 17 does not change the indicator B.

In other words, in a case in which the control unit 17 recognizes the state of riding in an automobile based on a result of detection by the acceleration sensor 16, then changes (updates) the indicator C, and thereafter recognizes the state of riding on a bicycle without recognizing the state of walking, the control unit 17 determines the recognition as misrecognition, and does not change the indicator B. In this case, the control unit 17 changes (updates) the indicator C.

Therefore, for example, in a situation where the user continues riding in an automobile, even if the automobile jiggles due to a poor road surface condition, the mobile telephone device 1 does not incorrectly determine that the user is riding on a bicycle, but can accurately display each state. The mobile telephone device 1 can accurately display each state, and thus can accurately calculate calories consumed by the user per day, for example.

The mobile telephone device 1 includes the control unit 17 that recognizes the first movement state, the second movement state, and the third movement state, based on acceleration. According to such a configuration, the control unit 17 recognizes the third movement state after recognizing the first movement state subsequent to the second movement state, and the control unit 17 recognizes the second movement state after recognizing the first movement state subsequent to the third movement state.

For example, the control unit 17 recognizes the state of riding in an automobile after recognizing the state of walking subsequent to the state of riding on a bicycle; and the control unit 17 recognizes the state of riding on a bicycle after recognizing the state of walking subsequent to the state of riding in an automobile. In other words, the control unit 17 does not recognize the state of riding in an automobile immediately after the state of riding on a bicycle; and the control unit 17 does not recognize the state of riding on a bicycle immediately after the state of riding in an automobile.

Therefore, for example, in a situation where the user continues riding in an automobile, even if the automobile jiggles due to a poor road surface condition, the mobile telephone device 1 does not incorrectly determine that the user is riding on a bicycle, but can accurately display each state.

Despite the fact that the user is continuously riding on a light automobile or a motorized bicycle, the control unit 17 may incorrectly determine that a state at a certain interval is the state of riding on a bicycle, due to determination based on a result of detection by the acceleration sensor 16.

In general, in a case in which a person transfers from an automobile to a bicycle, the person stops the automobile, walks to a place where the bicycle is parked, and rides on the bicycle. In this way, a walking action inevitably occurs between the automobile and the bicycle.

By detecting a walking action, the mobile telephone device 1 according to the present embodiment detects that the type of a vehicle is changed, thereby correcting incorrect determination.

As one of several patterns of correcting incorrect determination, incorrect determination is corrected to a true result by employing a type of a vehicle whose determination duration is the longest in terms of the total duration of detecting vehicles. The timing of correction may be real time, or may be when a predetermined period of time has elapsed.

Descriptions are hereinafter provided for a plurality of patterns of correcting incorrect determination with reference to FIGS. 5 to 7.

Pattern 1

In Pattern 1, in reality, the user is riding on a bicycle. As shown in FIG. 5A, the mobile telephone device 1 determines that the state is the state of riding on a bicycle, based on a result of detection by the acceleration sensor 16. Since the determination coincides with the reality and is correct, the determination need not be corrected.

Pattern 2

In Pattern 2, in reality, the user is riding in a light automobile or on a motorized bicycle.

As shown in FIG. 5B, the mobile telephone device 1 determines that the state is the state of riding on another type of vehicle (a light automobile or a motorized bicycle). Since the determination coincides with the reality and is correct, the determination need not be corrected.

As shown in FIG. 6A, the mobile telephone device 1 determines that the state is the state of riding on another type of vehicle until time t1, and determines that the state is the state of riding on a bicycle after the time t1, based on change of the road surface condition, etc.

In such a case, since the state of walking is not recognized between the state of riding on another type of vehicle and the state of riding on a bicycle, the mobile telephone device 1 determines one of the recognition to be incorrect. Since the duration of riding on another type of vehicle is the longest in percentage in the total duration (for example, 15 minutes), the mobile telephone device 1 corrects the state after the time t1 to the state of riding on another type of vehicle.

As shown in FIG. 6B, the mobile telephone device 1 determines that the state is the state of riding on a bicycle until the time t1, and determines that the state is the state of riding on another type of vehicle after the time t1, based on change of the road surface condition, etc.

In such a case, since the state of walking is not recognized between the state of riding on a bicycle and the state of riding on another type of vehicle, the mobile telephone device 1 determines one of the recognition to be incorrect. Since the duration of riding on another type of vehicle is the longest in percentage in the total duration (for example, 15 minutes), the mobile telephone device 1 corrects the state before the time t1 to the state of riding on another type of vehicle.

As shown in FIG. 6C, the mobile telephone device 1 determines that the state is the state of riding on a bicycle until the time t1 (hereinafter referred to as determination 1); determines that the state is the state of riding on another type of vehicle from the time t1 to time t2 based on change of the road surface condition, etc. (hereinafter referred to as determination 2); determines that the state is the state of riding on a bicycle from the time t2 to time t3 based on change of the road surface condition, etc. (hereinafter referred to as determination 3); determines that the state is the state of riding on another type of vehicle from the time t3 to time t4 based on change of the road surface condition, etc. (hereinafter referred to as determination 4); and determines that the state is the state of riding on a bicycle after time t4 based on change of the road surface condition, etc. (hereinafter referred to as determination 5).

In such a case, since the state of walking is not recognized between the state of riding on a bicycle and the state of riding on another type of vehicle, and between the state of riding on another type of vehicle and the state of riding on a bicycle, the mobile telephone device 1 determines that the determination 1 to 5 includes incorrect determination. Since the duration of riding on another type of vehicle is the longest in percentage in the total duration (for example, 15 minutes), the mobile telephone device 1 corrects the states in all the duration to the state of riding on another type of vehicle.

Pattern 3

In Pattern 3, in reality, the user gets off a light automobile or a motorized bicycle at the time t1, walks to a place where a bicycle is parked, and then transfers to the bicycle.

As shown in FIG. 7A, the mobile telephone device 1 firstly determines that the state is the state of riding on another type of vehicle, then detects interruption indicating the state of walking at the time t1 (hereinafter referred to as a walking interruption), and thereafter determines that the state is the state of riding on a bicycle.

A walking interruption is generated when the walking is stably detected (for example, when the user moves approximately 10 steps). Therefore, the timing of detecting a walking interruption is not exactly at the time t1, but is when the user moves approximately 10 steps from the time t1.

The mobile telephone device 1 traces the time of detecting a walking interruption back approximately 10 steps, and determines the duration from the time thus traced back until when the user starts moving on a bicycle, etc. to be in the state of walking. The "approximately 10 steps" is an example, and the present invention is not limited thereto.

In this manner, the mobile telephone device 1 can accurately detect a transfer from another type of vehicle to a bicycle, based on detection of a walking interruption.

Pattern 4

In Pattern 4, in reality, the user gets off a bicycle at the time t1, walks to a place where a light automobile or a motorized bicycle is parked, and then transfers to the light automobile or the motorized bicycle.

As shown in FIG. 7B, the mobile telephone device 1 firstly determines that the state is the state of riding on a bicycle, then detects a walking interruption at the time t1, and thereafter determines that the state is the state of riding on another type of vehicle.

In this manner, the mobile telephone device 1 can accurately detect a transfer from a bicycle to another type of vehicle, based on detection of a walking interruption.

Pattern 5

In Pattern 5, in reality, the user gets off a bicycle at the time t1, walks to a place where a light automobile or a motorized bicycle is parked, and then transfers to the light automobile or the motorized bicycle; gets off the light automobile or the motorized bicycle at the time t2, walks to the place where the bicycle is parked, and then transfers to the bicycle; gets off the bicycle at the time t3, walks to the place where the light automobile or the motorized bicycle is parked, and then transfers to the light automobile or the motorized bicycle; and gets off the light automobile or the motorized bicycle at the time t4, walks to the place where the bicycle is parked, and then transfers to the bicycle.

As shown in FIG. 7C, the mobile telephone device 1 firstly determines that the state is the state of riding on a bicycle; detects a walking interruption at the time t1, and thereafter determines that the state is the state of riding on another type of vehicle; detects a walking interruption at the time t2, and thereafter determines that the state is the state of riding on a bicycle; detects a walking interruption at the time t3, and thereafter determines that the state is the state of riding on another type of vehicle; and detects a walking interruption at the time t4, and thereafter determines that the state is the state of riding on a bicycle.

In this way, by detecting a walking interruption, the mobile telephone device 1 can detect that a type of vehicle is changed, and therefore can accurately detect a transfer from a bicycle to another type of vehicle, and a transfer from another type of vehicle to a bicycle.

Figure 8:
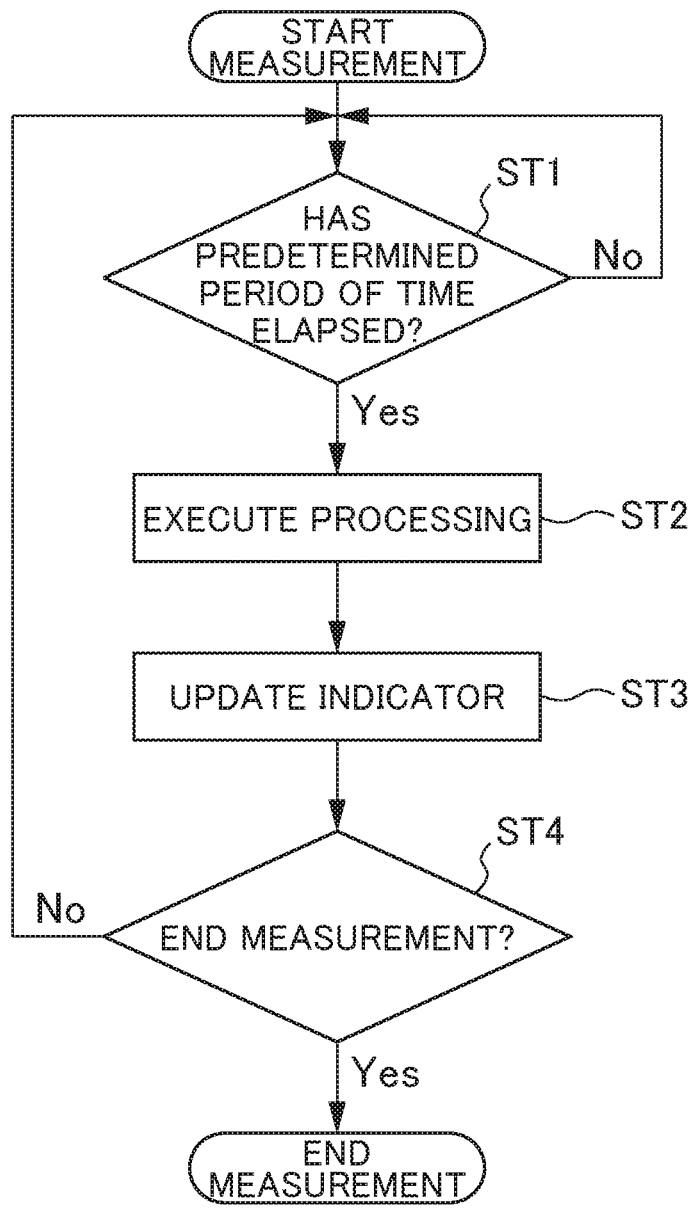
FIG. 8 is a flowchart illustrating a flow of operations of the mobile telephone device.

Next, descriptions are provided for a flow of operations of the mobile telephone device 1 with reference to a flowchart shown in FIG. 8. In the descriptions of the following embodiment, a determination result is corrected when a predetermined period of time has elapsed; however, the present invention is not limited thereto, and a determination result may be corrected in real time. The mobile telephone device 1 activates a predetermined application in response to the user's operation, starts measurement in response to an operation to start measurement, and ends the measurement in response to an operation to end the measurement; however, the present invention is not limited thereto. For example, the mobile telephone device 1 may start measurement at start time as specified by a timer, and may end the measurement at finish time as specified by the timer.

In Step ST1, the control unit 17 determines whether a predetermined period of time has elapsed. In a case of determining that the predetermined period of time has elapsed (YES), the processing advances to Step ST2; and in a case of determining that the predetermined period of time has not elapsed (NO), the processing in Step ST1 is repeated. The predetermined period of time can be arbitrarily set to, for example, several seconds, several minutes, several hours, or the like.

In Step ST2, the control unit 17 executes processing. More specifically, the control unit 17 determines each state based on a result of detection by the acceleration sensor 16, and executes necessary correction depending on presence or absence of a walking interruption.

In Step ST3, the control unit 17 updates the indicator on the display unit 11, based on a result of the processing in Step ST2. More specifically, the control unit 17 updates the indicators A to D shown in FIG. 4.

In Step ST4, the control unit 17 determines whether an operation to end the measurement is accepted. In a case in which an operation to end the measurement is accepted (YES), the measurement is ended; and in a case in which an operation to end the measurement is not accepted (NO), the processing returns to Step ST1.

In this manner, the mobile telephone device 1 can accurately display each state including the state of walking. The mobile telephone device 1 can accurately display each state, and thus can accurately calculate calories consumed by the user per day, for example.

In the above embodiment, the third movement state has been described as a state of moving in an automobile as transportation other than a bicycle; however, the present invention is not limited thereto, and the third movement state may be a state of moving in a train, a bullet train, a bus, or an automobile of any other particular type.

In the above embodiment, the second movement state has been described as a state of moving on a bicycle, and the third movement state has been described as a state of moving by transportation other than a bicycle; however, the present invention is not limited thereto. The second movement state may be a state of moving by a specific transportation (for example, a train or an automobile) other than a bicycle, and the third movement state may be a state of moving by transportation other than the specific transportation.

What is claimed is:

1. An electronic device, comprising:
   a controller configured to:
   determine that a state is: a first movement state as a state of walking; a second movement state as a state of moving on a bicycle; or a third movement state as a state of moving by transportation other than the bicycle, based on acceleration;
   integrate determination duration of each of the first movement state, the second movement state, and the third movement state; and cause a display to display integrated duration of each of the first movement state, the second movement state, and the third movement state, based on the integrated determination duration;

wherein, in a case in which the controller determines that a state is any one state of the second movement state and the third movement state, if the preceding state, which is determined to be the one state, is the first movement state, the controller determines that the one state is a valid movement state, and causes the display to incrementally display the integrated duration of the one state that has been determined as the valid movement state.

2. The electronic device according to claim 1, wherein, after the controller determines that the one state is a valid movement state, and after the controller detects that the determination of the one movement state has changed to determination of an other movement state, skipping the first movement state, the controller corrects the valid movement state, and corrects the displaying of the integrated duration of the second movement state and the third movement state, based on comparison between lengths of determination duration of the one state and the other state.

3. The electronic device according to claim 2, wherein, in a case in which the other state is longer than the one state in a comparison between lengths of determination duration, the controller corrects the valid movement state to the other state, and corrects the displaying of the integrated duration of the second movement state and the third movement state, by deeming that the determination duration of the one state is the determination duration of the other state.

4. The electronic device according to claim 3, wherein, in a case in which the one state is longer than the other state in a comparison between lengths of determination duration, the controller maintains the valid movement state as the one state, and corrects the displaying of the integrated duration of the second movement state and the third movement state, by deeming that the determination duration of the other state is the determination duration of the one state.

5. The electronic device according to claim 1, wherein, when the controller determines that a state is the first movement state, the controller adds predetermined duration to the integrated determination duration, and causes the display to display the integrated duration.

6. An electronic device, comprising:

a controller configured to:

determine that a state is any of a first movement state, a second movement state, or a third movement state, based on acceleration;

integrate determination duration of each of the first movement state, the second movement state, and the third movement state; and cause a display to display integrated duration of each of the first movement state, the second movement state, and the third movement state, based on the integrated determination duration;

wherein, in a case in which the controller determines that a state is any one state of the second movement state and the third movement state, if the preceding state, which is determined to be the one state, is the first movement state, the controller determines that the one state is a valid movement state, and causes the display to incrementally display the integrated duration of the one state that has been determined as the valid movement state; and wherein, after the controller determines that the one state is a valid movement state, and after the controller detects that the determination of the one movement state has changed to determination of an other movement state, skipping the first movement state, the controller corrects the valid movement state, and corrects the displaying of the integrated duration of the second movement state and the third movement state, based on comparison between lengths of determination duration of the one state and the other state.

7. The electronic device according to claim 6, wherein, in a case in which the other state is longer than the one state in a comparison between lengths of determination duration, the controller corrects the valid movement state to the other state, and corrects the displaying of the integrated duration of the second movement state and the third movement state, by deeming that the determination duration of the one state is the determination duration of the other state.

8. The electronic device according to claim 7, wherein, in a case in which the one state is longer than the other state in a comparison between lengths of determination duration, the controller maintains the valid movement state as the one state, and corrects the displaying of the integrated duration of the second movement state and the third movement state, by deeming that the determination duration of the other state is the determination duration of the one state.

9. The electronic device according to claim 6, wherein, when the controller determines that a state is the first movement state, the controller adds predetermined duration to the integrated determination duration, and causes the display to display the integrated duration.

10. A method for displaying a state, the method configured for a controller of an electronic device to determine that a state is a first movement state as a state of walking; a second movement state as to state of moving on a bicycle; or a third movement state as a state of moving by transportation other than the bicycle, based on acceleration;

integrate determination duration of each of the first movement state, the second movement state, and the third movement state; and cause a display to display integrated duration of each of the first movement state, the second movement state, and the third movement state, based on the integrated determination duration;

wherein, in a case in which the controller determines that a state is any one state of the second movement state and the third movement state, if the preceding state, which is determined to be the one state, is the first movement state, the controller determines that the one state is a valid movement state, and causes the display to incrementally display the integrated duration of the one state that has been determined as the valid movement state.

11. A non-transitory computer-readable medium storing a program for causing a controller of an electronic device to:

determine that a state is: a first movement state as a state of walking; a second movement state as a state of moving on a bicycle; or a third movement state as a state of moving by transportation other than the bicycle, based on acceleration;

integrate determination duration of each of the first movement state, the second movement state, and the third movement state; and cause a display to display integrated duration of each of the first movement state, the second movement state, and the third movement state, based on the integrated determination duration;

wherein, in a case in which the controller determines that a state is any one state of the second movement state and the third movement state, if the preceding state, which is determined to be the one state, is the first movement state, the controller determines that the one state is a valid movement state, and causes the display to incrementally display the integrated duration of the one state that has been determined as the valid movement state.

* * * * *